US009220411B2

(12) United States Patent
Hillman

(10) Patent No.: US 9,220,411 B2
(45) Date of Patent: Dec. 29, 2015

(54) IN-VIVO OPTICAL IMAGING METHOD INCLUDING ANALYSIS OF DYNAMIC IMAGES

(75) Inventor: Elizabeth M.C. Hillman, New York, NY (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 1409 days.

(21) Appl. No.: 12/302,986

(22) PCT Filed: May 31, 2007

(86) PCT No.: PCT/US2007/013024
§ 371 (c)(1),
(2), (4) Date: Mar. 26, 2009

(87) PCT Pub. No.: WO2007/143141
PCT Pub. Date: Dec. 13, 2007

(65) Prior Publication Data
US 2009/0252682 A1 Oct. 8, 2009

Related U.S. Application Data

(60) Provisional application No. 60/809,860, filed on Jun. 1, 2006, provisional application No. 60/809,861, filed on Jun. 1, 2006, provisional application No. 60/897,259, filed on Jan. 24, 2007.

(51) Int. Cl.
A61B 6/00 (2006.01)
A61B 5/00 (2006.01)
A61K 49/00 (2006.01)

(52) U.S. Cl.
CPC ............ A61B 5/0059 (2013.01); A61B 5/415 (2013.01); A61B 5/418 (2013.01); A61K 49/0017 (2013.01); A61B 2503/40 (2013.01)

(58) Field of Classification Search
None
See application file for complete search history.

(56) References Cited

U.S. PATENT DOCUMENTS

| 4,972,331 | A | * | 11/1990 | Chance | 600/310 |
| 5,485,530 | A | * | 1/1996 | Lakowicz et al. | 382/191 |
| 5,672,881 | A | * | 9/1997 | Striepeke et al. | 250/461.2 |
| 5,699,798 | A | * | 12/1997 | Hochman et al. | 600/420 |
| 5,784,145 | A | * | 7/1998 | Ghodse et al. | 351/205 |
| 5,784,162 | A | * | 7/1998 | Cabib et al. | 356/456 |

(Continued)

FOREIGN PATENT DOCUMENTS

WO    WO 03/006966    1/2003

OTHER PUBLICATIONS

Texier et al. "Luminescent Probes for Optical In Vivo Imaging" SPIE 5704:16-22 (2005).

Primary Examiner — Nicholas Evoy
(74) Attorney, Agent, or Firm — Occhiuti & Rohlicek LLP

(57) ABSTRACT

In-vivo optical molecular imaging methods for producing an image of an animal are described. A time series of image data sets of an optical contrast substance in the animal is acquired using an optical detector Each image data set is obtained at a selected time and has the same plurality of pixels, with each pixel having an associated value. The image data sets are analyzed to identify a plurality of distinctive time courses, and respective pixel sets are determined from the plurality of pixels which correspond to each of the time courses. In one embodiment, each pixel set is associated with an identified anatomical or other structure, and an anatomical image map of the animal can be generated which includes one or more of the anatomical structures.

22 Claims, 8 Drawing Sheets

(56) References Cited

U.S. PATENT DOCUMENTS

| | | | | |
|---|---|---|---|---|
| 5,817,462 A * | | 10/1998 | Garini et al. | 506/9 |
| 5,936,731 A * | | 8/1999 | Cabib et al. | 356/456 |
| 5,976,825 A * | | 11/1999 | Hochman | 435/29 |
| 5,995,645 A * | | 11/1999 | Soenksen et al. | 382/133 |
| 6,055,451 A * | | 4/2000 | Bambot et al. | 600/476 |
| 6,057,163 A * | | 5/2000 | McMillan | 436/172 |
| 6,081,612 A * | | 6/2000 | Gutkowicz-Krusin et al. | 382/128 |
| 6,160,618 A * | | 12/2000 | Garner | 356/318 |
| 6,175,655 B1 * | | 1/2001 | George et al. | 382/257 |
| 6,208,749 B1 * | | 3/2001 | Gutkowicz-Krusin et al. | 382/128 |
| 6,208,886 B1 * | | 3/2001 | Alfano et al. | 600/473 |
| 6,241,672 B1 * | | 6/2001 | Hochman et al. | 600/431 |
| 6,276,798 B1 * | | 8/2001 | Gil et al. | 351/206 |
| 6,293,911 B1 * | | 9/2001 | Imaizumi et al. | 600/160 |
| 6,320,196 B1 * | | 11/2001 | Dorsel et al. | 250/458.1 |
| 6,415,172 B1 * | | 7/2002 | Painchaud et al. | 600/407 |
| 6,529,768 B1 * | | 3/2003 | Hakamata | 600/476 |
| 6,564,088 B1 * | | 5/2003 | Soller et al. | 600/478 |
| 6,573,063 B2 * | | 6/2003 | Hochman | 435/29 |
| 6,615,063 B1 * | | 9/2003 | Ntziachristos et al. | 600/312 |
| 6,630,127 B2 * | | 10/2003 | Renshaw et al. | 424/9.3 |
| 6,671,540 B1 * | | 12/2003 | Hochman | 600/431 |
| 6,748,259 B1 * | | 6/2004 | Benaron et al. | 600/476 |
| 6,834,238 B1 * | | 12/2004 | Hochman | 702/21 |
| 6,975,899 B2 * | | 12/2005 | Faupel et al. | 600/476 |
| 7,006,676 B1 * | | 2/2006 | Zeylikovich et al. | 382/131 |
| 7,035,450 B1 * | | 4/2006 | Muller et al. | 382/154 |
| 7,047,064 B1 * | | 5/2006 | Zavislan et al. | 600/476 |
| 7,054,002 B1 * | | 5/2006 | Sevick-Muraca et al. | 356/317 |
| 7,117,098 B1 * | | 10/2006 | Dunlay et al. | 702/21 |
| 7,179,222 B2 * | | 2/2007 | Imaizumi et al. | 600/109 |
| 7,181,267 B2 * | | 2/2007 | Barbato | 600/478 |
| 7,280,726 B2 * | | 10/2007 | Fox | 385/104 |
| 7,328,059 B2 * | | 2/2008 | Sevick-Muraca et al. | 600/473 |
| 7,333,647 B2 * | | 2/2008 | Boas et al. | 382/131 |
| 7,383,076 B2 * | | 6/2008 | Ntziachristos et al. | 600/473 |
| 7,530,947 B2 * | | 5/2009 | Yokomise et al. | 600/160 |
| 7,548,272 B2 * | | 6/2009 | Perlman et al. | 348/371 |
| 7,567,293 B2 * | | 7/2009 | Perlman et al. | 348/371 |
| 7,599,732 B2 * | | 10/2009 | Sevick-Muraca et al. | 600/476 |
| 8,016,419 B2 * | | 9/2011 | Zhang et al. | 351/206 |
| 8,068,899 B2 * | | 11/2011 | Llewellyn et al. | 600/478 |
| 8,619,237 B2 * | | 12/2013 | Hillman et al. | 356/2 |
| 2004/0019283 A1 * | | 1/2004 | Lambert et al. | 600/476 |
| 2004/0208385 A1 * | | 10/2004 | Jiang | 382/254 |
| 2004/0209237 A1 * | | 10/2004 | Flewelling et al. | 435/4 |
| 2004/0220479 A1 * | | 11/2004 | Wake et al. | 600/476 |
| 2005/0054936 A1 * | | 3/2005 | Balas | 600/476 |
| 2005/0065440 A1 * | | 3/2005 | Levenson | 600/476 |
| 2006/0013454 A1 * | | 1/2006 | Flewelling et al. | 382/128 |
| 2006/0119865 A1 * | | 6/2006 | Hoyt et al. | 356/625 |
| 2006/0184043 A1 * | | 8/2006 | Tromberg et al. | 600/476 |
| 2006/0285635 A1 * | | 12/2006 | Boppart et al. | 378/22 |
| 2009/0252682 A1 * | | 10/2009 | Hillman | 424/9.1 |
| 2010/0168586 A1 * | | 7/2010 | Hillman et al. | 600/476 |
| 2012/0140240 A1 * | | 6/2012 | Hillman et al. | 356/496 |

\* cited by examiner

IN-VIVO OPTICAL IMAGING METHOD INCLUDING ANALYSIS OF DYNAMIC IMAGES

CROSS REFERENCES TO RELATED APPLICATIONS

This application is based on U.S. provisional patent application Ser. No. 60/809,860, filed Jun. 1, 2006 and titled "Method and Device for Identification of Organ Location in Molecular Imaging", Ser. No. 60/809,861, filed on Jun. 1, 2006, and Ser. No. 60/897,259, filed on Jan. 24, 2007, and titled "Method and Device for Identification of Organ Location in Molecular Imaging".

GOVERNMENT SUPPORT

This invention was made with Government support under Grant Nos. EB000790, EB000768, and NS051188 awarded by the National Institutes of Health. The Government has certain rights in this invention.

FIELD OF THE INVENTION

The invention relates to an optical molecular imaging method for imaging animals including the acquisition of an in-vivo time series of images of at least one optical contrast substance, and the analysis of those images.

BACKGROUND OF THE INVENTION

In-vivo molecular imaging is a rapidly advancing field, impacting drug development and testing, research into disease processes, and potentially clinical diagnostic imaging. Optical molecular imaging is a method in which an optical contrast substance is introduced to or activated within an animal, and the resultant signal due to the optical contrast substance, (such as light being absorbed or emitted, whether in a UV, visible or infrared range) is measurable using an optical detector such as a camera to provide one or more images.

For example, optical molecular probes are available which can include fluorescent or luminescent dyes, or absorbing substances, and can be used to target and label specific cell types or activate biochemical processes like bioluminescence. Molecular probes can also be generated by cells in animals transgenically or otherwise altered to do so. Optical molecular imaging, as compared to magnetic resonance imaging (MRI), x-ray or positron-emission imaging, benefits from the fact that such fluorescent, luminescent or absorbing substances can be small, biocompatible molecules.

Optical molecular probes are generally of the following three types: 1) injectable (or otherwise introduced), which are designed to accumulate at the location of a particular target, 2) expressed, via transgenic mutation, or 3) transplanted, following labeling in-vitro of particular cell types. Probes can be normally fluorescent, luminescent or absorbing, or can be activatable, i.e., can change their optical properties in response to environment change.

Many different types of fluorescent and luminescent dyes are available for incorporation into molecular probes including organic and nanoparticle based dyes. Fluorescent dyes require excitation at an appropriate wavelength range for light emission, with the emitted light occurring in a different wavelength range than the excitation range. Luminescent dyes do not require excitation. Recent efforts have focused on the development of dyes which excite and/or emit in the near-infrared (NIR) region, where scattering and absorption in tissue is significantly less, enabling improved penetration and resolution.

In-vivo optical molecular imaging is typically performed on small animals to study the physiologic, pathologic or pharmacologic effects of various drugs or diseases. Molecular imaging can also be performed on humans, and it is hoped that molecular imaging will eventually provide substantial advances in diagnostic imaging. The benefits of in-vivo imaging of small animals are significant because it allows processes and responses to be visualized in real-time in their native environments, and allows longitudinal studies to be performed using the same small animal over time, allowing evaluation of disease progression or response to treatment. Further, in-vivo imaging of small animals reduces the number of animals required for a study, and can reduce the variance in studies where disease manifestation varies from animal to animal, such as cancers in-situ.

However, in-vivo optical molecular imaging presents many challenges. The main challenge is overcoming the effects of light scatter and absorption. For example, when a fluorescent or luminescent dye is used to label specific cells, because the cells can be located deep within the body, the light emitted from them will undergo optical scattering because of intervening matter, which is more problematic the deeper the labeled cells are within the body. Thus, unless the labeled cells are located near the outer surface of the animal, the scatter and absorption of light distorts and attenuates the signals emanating therefrom such that the localization, quantification, and host organ identification of the signals can be very difficult. These effects can distort the apparent shape and location of these targeted labeled cells.

One approach to overcome the problems associated with light scattering involves the use of subcutaneous xenografts (or transplanted cells or tissue) whose superficial location simplifies the localization of labeled cells. However, for transplanted cancer cells, xenografts often do not resemble the human disease, as these cells are often surrounded by a pseudo-capsule, have limited chances to invade major anatomical structures, and rarely spread metastasis. Thus, the study of orthotopic disease models, i.e., cells in their native location, is generally preferred.

Another problem associated with the use of fluorescent and luminescent molecular probes is that these are generally designed such that measurable light signals emanate from the labeled cells, with little or no detectable signals emanating from adjacent tissue or organs, so that the localization of the labeled cells is often uncertain. In the absence of a non-invasive tool for verifying the anatomical location thereof, scientists are limited to ex-vivo histological examination of the labeled cells. This can significantly increase study cost and time, and can degrade data owing to inter-animal variability.

Further, auto-fluorescence and non-specific labeling within the body confounds attempts to identify the true location of labeled cells. Auto-fluorescence arises from intrinsic fluorophores such as tryptophan, collagen, NADH and porphyrins, and also from chemicals in many common animal foods, causing marked fluorescence in the intestines. Multispectral optical imaging has been used to improve image contrast and isolate signals from the labeled cells in the presence of auto-fluorescence. These multispectral imaging systems are typically implemented using a plurality of optical fixed filters or alternatively tunable filters positioned in front of an optical detector to allow light within a predetermined wavelength range to be recorded, and to record a series of images at different wavelength ranges. Other means of multispectral imaging including dispersive and snapshot systems are also applicable. The resulting image sets are equivalent to each image pixel having its own emission spectrum. Analysis can be performed to separate pixels with differing spectral signatures and hence different constituent fluorophores. For example, this approach has been implemented by Cambridge Research Instruments (CRI Maestro™ Woburn Mass.) using liquid crystal tunable filters positioned in front of a CCD camera.

Various three dimensional (3D) imaging systems have also been developed to overcome some of these difficulties, including for example Xenogen's IVIS Imaging System 3D series, which uses optical tomography for imaging small animals such as mice. Such systems rely on making many measurements between light sources and detectors where the relative positions are varied to create a tomographic data set. To create 3D images, an image reconstruction algorithm is required which utilizes a simulation of the likely scattered propagation of light through the tissue based on its geometry and estimated background optical properties. The motivations for creating 3D images of the distribution of a molecular probe within the animal include the desire for 3D localization of the contrast in the animal to aid in interpretation of its anatomical position. However, such systems are highly complex, expensive, and still suffer from a lack of landmark anatomical structures to allow the actual anatomical location of the labeled cells to be identified. While the IVIS Imaging System offers a generic computerized 3D mouse anatomical atlas to overlay with acquired image data to aid in organ identification, matching generic anatomy to each individual mouse is not always accurate and is highly sensitive to mouse age, size, repositioning, and any distortions within the optical images.

Other multi-modality imaging systems have also been developed which combine optical imaging with other imaging modalities such as x-ray, micro-CT, magnetic resonance imaging (MRI), or ultrasound. Such systems significantly increase the cost and complexity of the imaging process, especially when simultaneous image acquisition is attempted. In addition, x-ray contrast of bone and the non-specific contrast of ultrasound will not provide good delineation of the internal soft tissue organs. Since the imaging radiation and geometries are also different between modalities, co-registration with the optical images is problematic.

Various known approaches to optical molecular imaging are described below, with these descriptions also including descriptions of various optical contrast substances which can be optically imaged. These descriptions are not inclusive of all possible embodiments of this invention. In one approach, it is possible to conjugate optical dyes to active molecules such as peptides and antibodies that will specifically bind to targeted cell types. These targeted fluorophore probes are then injected, usually intravenously, and localize at the site of the target. For example, under-glycosylated mucin-1 antigen (uMUC-1) is overexpressed in greater than 90% of human breast, ovarian, pancreatic, colorectal, lung, prostate, colon and gastric carcinomas. A uMUC-1 targeting molecular probe has been developed which carries two fluorescent molecules (FITC and Cy5.5) in addition to a cross-linked iron oxide (CLIO) particle which provides magnetic resonance imaging (MRI) contrast. Mice can be subcutaneously implanted with both uMUC-1 positive and uMUC-1 negative tumors, and then injected with the uMUC-1 targeted probe approximately 24 hours prior to MRI and then optical imaging with a commercially available two dimensional imaging system. Both imaging modalities show good localization of the probe to the uMUC-1 positive tumors.

Labeled cell transplantation is a method that includes labeling specific live cells in-vitro and then transplanting them in-vivo, and provides a way to study cell migration, such as the circulation of tumor cells in the blood stream, or for investigating responses of cells in their native environments to pharmacology or interventions. In this approach, the need for target specificity is reduced. This method is feasible for longitudinal imaging of the migration of cy5.5 (optical)+ CLIO (MRI) labeled, transplanted human pancreatic islet cells in-vivo. Islet transplantation into the liver is a promising human treatment for diabetes. By transplanting labeled cells into the kidney capsule or liver of mice, their migration and viability can be longitudinally monitored in-vivo.

Activatable fluorescence is the use of fluorescent molecular probes that become fluorescent in the presence of a particular molecule such as enzyme. For example, to evaluate the role of protease cathepsin-B expression in tumor invasion of 9L gliosarcomas, a cathepsin-B sensitive fluorescent probe can be injected intravenously a couple of weeks after implantation of such tumors into the brains of mice. Approximately sixteen hours after probe injection, sufficient fluorescence can be detected to visualize the tumors non-invasively in-vivo and confirming cathepsin-B expression.

Transgenic bioluminescence is a method wherein developed transgenic mice have localized expression of a bioluminescent enzyme, commonly luciferase. For prostate imaging, a prostate-specific antigen (PSA) promoter can be targeted to express luciferase, and a D-luciferin can be injected to react with luciferase to create bioluminescence at the site of luciferase expression. It is typical to wait approximately 25 minutes for this process to be complete before imaging, and to subtract background luminescence.

Transgenic fluorescence involves the use of varieties of green, yellow and red fluorescent proteins (GFP, YFP and RFP respectively for example) in transgenic animals. Specific cells can be targeted to express a fluorescent protein in normal or diseased animals. Transgenic expression of fluorescent molecules can be present from birth in genetically modified animals, but can also be achieved locally in-vivo using fluorescent protein-carrying adenoviruses. It is also possible to transplant transgenic tissues/cells into normal animals, where they continue to express their fluorescent proteins. In a recent study, mice expressing GFP driven by nestin, a stem cell marker expressed in nascent blood vessels, received orthotopic transplantation of RFP expressing human pancreatic tumor cells. An angiogenic inhibitor was given to a subset of the mice over 14 days until they were sacrificed. Ex-vivo microscopy of both the RFP and GFP allowed vessel growth and tumor growth to be evaluated independently.

SUMMARY OF THE INVENTION

In one aspect, the present invention relates to an optical molecular imaging method for in-vivo imaging of animals such as mice which provides contrast enhancement of a targeted region. In one embodiment, the method includes acquiring a time series of image data sets of an optical contrast substance in the animal using an optical detector such as a camera. The image data sets are analyzed to identify a plurality of distinctive time courses, and respective pixel sets are determined from the plurality of pixels which correspond to each of the time courses. Each of these pixel sets is associated with an identified structure, and an image of the animal is generated wherein a targeted region is delineated using the identified structures. For example, some of these identified structures can be subtracted from the final image to generate a more specific image of a targeted region, or the targeted region itself could be one of the identified structures.

As used herein, animal is intended to encompass humans. Further, as used herein, structures refer to any of a broad category of items which can be differentiated in the image data sets, including for example organs, lymph nodes, tumors, functional structures, blood vessel networks, disease perimeters, and so forth. This approach takes advantage of the fact that various structures play different roles in circulating, metabolizing, or retaining an optical contrast substance, and an evaluation of the dynamics thereof provides useful information to identify these structures. In other words, various structures will exhibit individual distinctive time courses of the light emitted (or absorbed) due to the optical contrast substance. By evaluating these dynamics in the animal, various different structures can be identified, and the generated image of a targeted region can be improved over what is shown in an acquired image.

Another aspect of the present invention relates to an in-vivo optical molecular imaging method for producing an anatomical image map of an animal. A time series of image data sets of an optical contrast substance in the animal is acquired using an optical detector, with each image data set obtained at a selected time and having the same plurality of pixels as the others. Each pixel in each image has an associated value. The image data sets are analyzed to identify a plurality of distinctive time courses, and each time course is associated with a respective anatomical structure of the animal. A respective pixel set is determined from the plurality of pixels which corresponds to each of the time courses, and each pixel set is associated with an identified anatomical structure. An anatomical image map of the animal is generated which includes each anatomical structure as a differentiated pixel set. The optical contrast agent can, for example, take the form of a dye which is introduced into an animal such as by injection.

In another aspect, the above method can be extended to incorporate the parallel use of another targeted (or other) optical contrast substance. Here a first optical contrast substance which is introduced or activated in a targeted region is used in parallel with a second optical contrast substance. For example, the first optical contrast substance can be a dye for labeling specific cells of the animal, labeled cells, or an activated optical contrast substance. A targeted image data set of the first optical contrast substance is acquired using an optical detector such as a camera. A time series of anatomical image data sets is acquired of the second optical contrast substance in the animal using the optical detector. The anatomical image data sets are analyzed to extract a plurality of anatomical structures, including for example specific organs of the animal, and an anatomical image map is generated including the extracted anatomical structures. This anatomical image map can be registered with the targeted image data set to produce a combined image to thereby localize the labeled cells with respect to the anatomical structures.

The discrimination between the different optical contrast substances can be achieved by imaging them at different times (i.e., a time-course for one optical contrast substance can be acquired, and then after a suitable time, a second optical contrast substance can be administered and imaged). Alternatively, two or more optical contrast substances can be administered simultaneously, and their signals discriminated using simple multi-spectral discrimination. In addition, multi-spectral imaging can be employed to remove autofluorescence and to further characterize autofluorescent and targeted structures. A plurality of wavelengths can be acquired rapidly and sequentially using a series of filters or a tunable filter, or alternatively, with multi-view or dispersive snapshot systems.

DETAILED DESCRIPTION OF THE PREFERRED EMBODIMENTS

Figure 1:
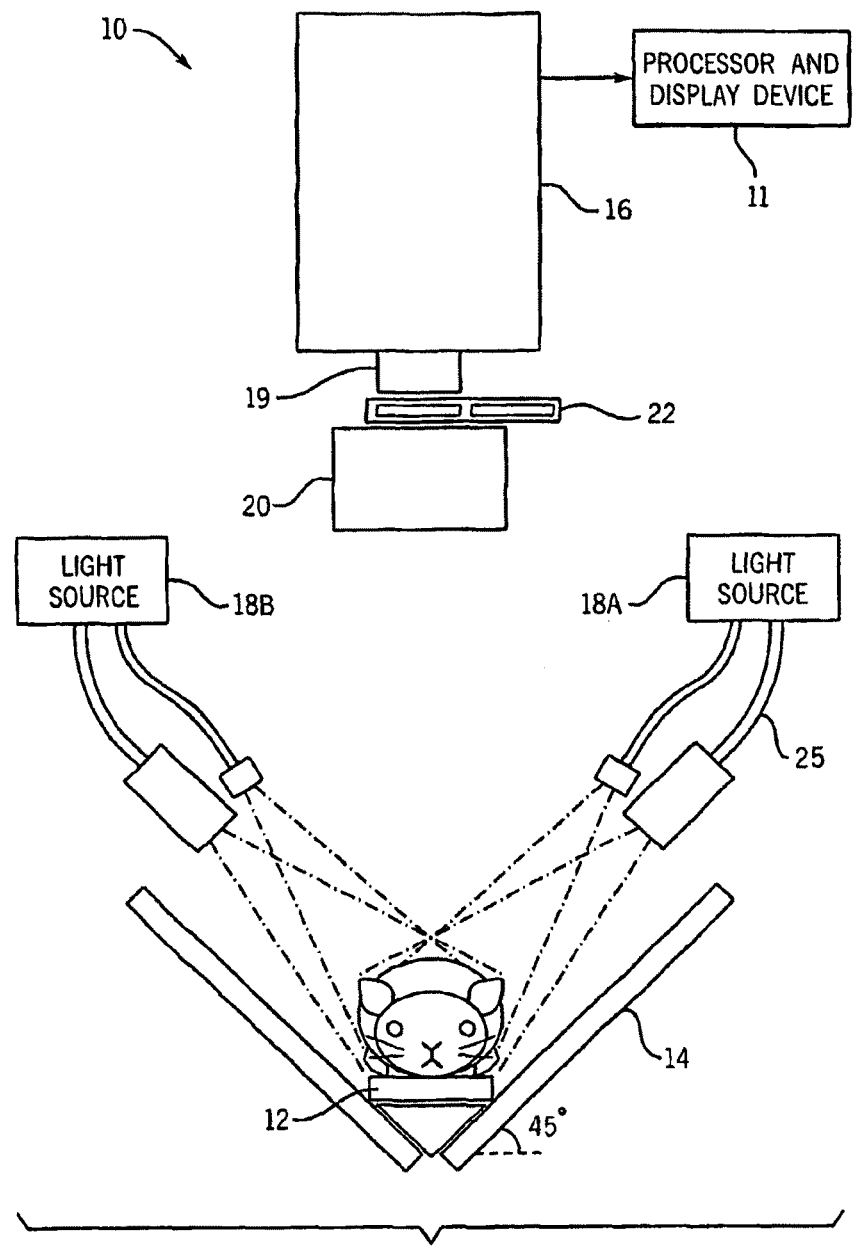
FIG. 1 is an example of an optical molecular imaging system for performing various methods described herein.

FIG. 1 illustrates one embodiment of a fluorescent dynamic optical imaging system 10 for imaging small animals such as mice. The imaging system 10 includes an optical detector 16 which is operable to acquire various images of the mouse. The imaging system 10 also includes a processor and display device 11 which is operable to generate and display other images of the mouse. These generated images can include an image of a targeted region, an anatomical image map which includes anatomical structures of the mouse, or a combined image of an anatomical image map and a targeted region, which shows a targeted region localized with respect to the anatomical structures. Both the acquired and generated images can be displayed on the display device 11.

Briefly, at least one optical contrast substance in the mouse is imaged with the imaging system 10 to acquire a time series of image data sets which are analyzed using the dynamics of the optical contrast substance to identify various anatomical or other structures. Any one of many different types of optical contrast substances can be used with the imaging methods described herein, including fluorescent, luminescent, or absorbing dyes, various optical molecular probes or labeled cells such as those described above, or other optical contrast substances such as hemoglobin which is an intrinsic absorber. The time series image data sets require a substance providing optical contrast which changes over time. The nature of the optical contrast substance will govern the behavior of the in-vivo dynamics. The identified anatomical or other structures are used in various ways as described below.

The system 10 also includes an imaging platform 12 for supporting a mouse in a desired arrangement, such as in a prone position or a supine position. In a preferred embodiment, mirrors 14 are arranged at 45 degree angles with respect to the imaging platform such that multiple views of the mouse, i.e., a top and/or bottom view, and side views of the mouse, are within the field of view of the optical detector 16, which is arranged above the imaging platform 12. Other embodiments can include other arrangements of optical detector 16 and mirrors to provide other views of the mouse. In one embodiment, the optical detector 16 is a cooled 14 bit charge coupled device (CCD) camera including a relay lens 19 and the field of view is approximately 9 cm by 9 cm. Thus, although the camera produces 2D images, these are "enhanced" 2D images since multiple views of the mouse are obtained.

One or more light sources 18A, 18B provide illumination of the mouse and/or provide excitation of any fluorescent dyes used as optical contrast substances within the mouse. The fluorescent dyes require excitation at an appropriate wavelength range for light emission or absorption, with the light emission or absorption occurring in a separate wavelength range, and these ranges depend on the specific type of dye selected.

Figure 2:
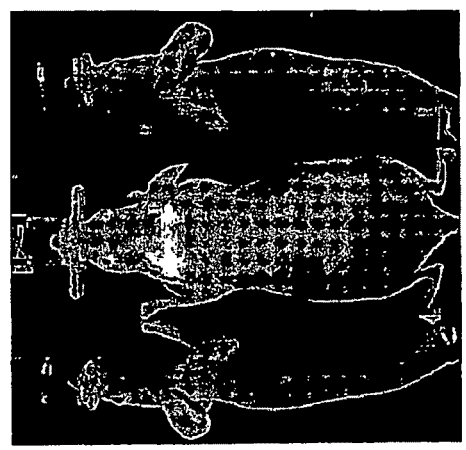
FIG. 2 is a gray scale bright field image of the mouse obtained by the camera of the optical imaging system of FIG. 1.

Light signals from the mouse enter the zoom lens 20 and can be filtered by a selected filter element of filter 22, which can be a liquid crystal tunable filter and/or incorporate a motorized filter changer. The filter 22 is tuned such that a desired range of light signals pass through to be recorded by the optical detector 16. The optical detector 16 is operable to acquire a plurality of desired image data sets, including a gray scale bright field image data set, which can be displayed as shown in FIG. 2.

By appropriate activation of the light sources 18A, 18B and tuning of the filter 22, system 10 is operable to record and store separately the light signals due to a single optical contrast substance or the light signals due to two or more optical contrast substances used in parallel, which can be stored as separate image data sets. The image data sets are then analyzed by the processor in a manner to be further described below.

Bifurcated liquid light guides 25 can be used to deliver light from the sources 18A, 18B to shine on the mouse. Other means can also be used. The light sources 18A, 18B and any corresponding filter elements are selected to have desired characteristics according to the optical contrast substances to be used in the imaging process. For example, when using a fluorescent dye such as indocyanine green (ICG) dye, light source 18A can include two laser diodes (160 mW total) to provide excitation light at 785 nm to excite the ICG dye. When using a fluorescent dye such as Dextran Texas Red dye, light source 18B can be a halogen light source, and a motorized filter wheel having a plurality of filter elements can be used to provide filtered light at a desired excitation wavelength range of 570 nm plus or minus 20 nm to excite the Dextran Texas Red dye. The respective light sources can be controlled by an electronic shutter in the 570 nm light path, or digital modulation of the laser diodes to allow synchronization of illumination with the filter elements, tunable filter, and image acquisition.

As mentioned, the tunable filter is tuned to allow passage of light signals having desired wavelengths while filtering out other unwanted signal wavelengths. For example, using a ICG dye or a Dextran Texas Red dye, the filter will be tuned to 600 nm or to 850 plus or minus 20 nm respectively be used to reject corresponding excitation light while allowing passage of desired emitted light. In other embodiments, the filter can be tuned to other wavelength ranges to obtain multispectral image data to for example, evaluate any autofluorescence of the mouse.

Figure 3:
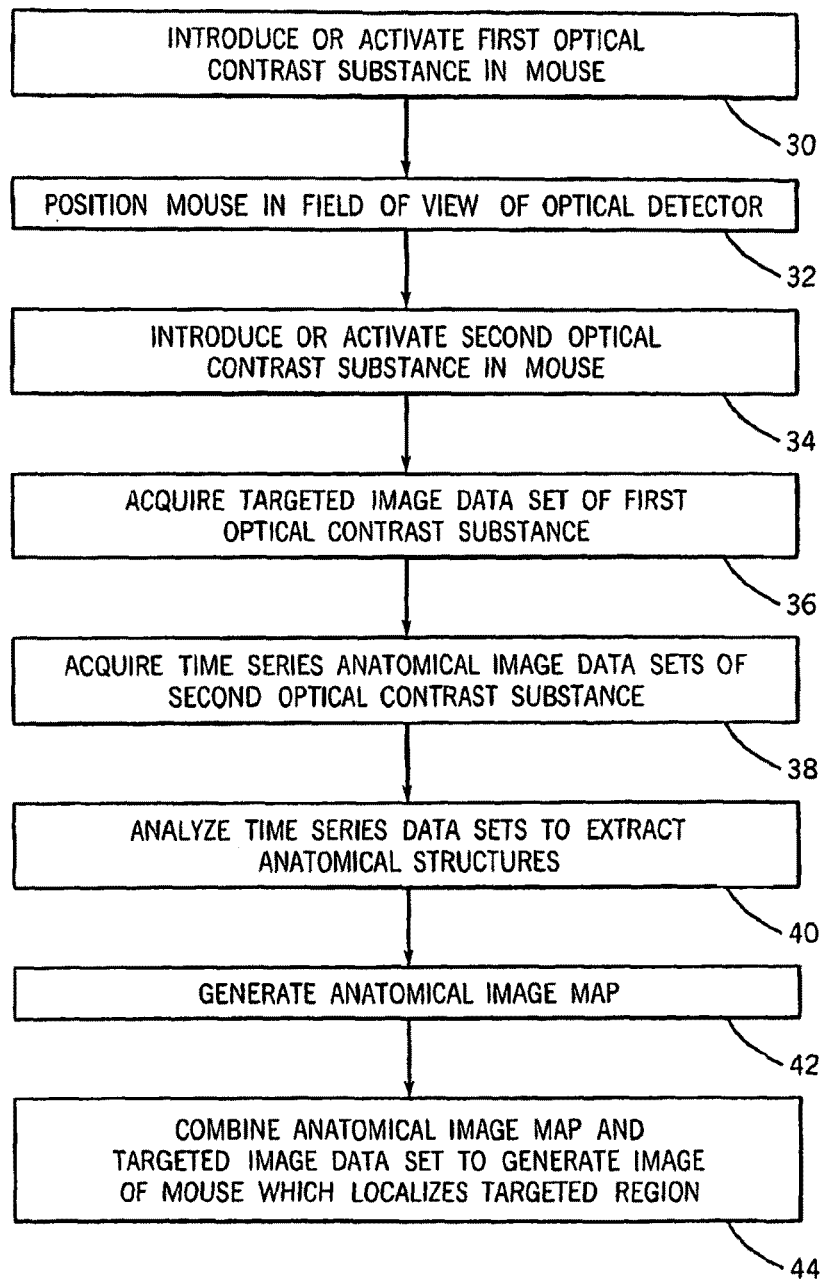
FIG. 3 is a flow chart of one embodiment of the method according to the invention.

FIG. 3 is a flow chart of one embodiment of a method practiced with the system of FIG. 1. The method generates an anatomical image map of an animal such as a mouse with delineated anatomical structures and further generates an image of the animal which shows a desired targeted region such as labeled cells combined with delineated anatomical structures of the animal such as organs. As explained more fully below, the order of the steps shown in this flow chart is not material, and in other embodiments these steps can be performed in a different order.

Thus, in one embodiment, as indicated at process block 30, a first optical contrast substance is introduced or activated in the mouse, where the first optical contrast substance includes a plurality of labeled cells or targets a desired targeted region. For example, the first optical contrast substance can be a targeted molecular probe which includes fluorescently labeled pancreatic islet cells which are transplanted into the kidney of the mouse. In another example, the first contrast agent can be a uMUC-1 targeted fluorescent molecular probe and orthotopically transplanted uMUC-1 positive tumors. Many other kinds of targeted molecular probes can also be used as the first optical contrast agent in the mouse.

At process block 32, the mouse is positioned in a desired arrangement in the field of view of the optical detector. For example, the mouse may be placed in a prone position or in a supine position on the imaging platform.

At process block 34, a second optical contrast substance is introduced or activated in the mouse. For example, a dye such as an ICG dye or a Dextran Texas Red dye can be used and can be injected into the tail vein of an anesthetized mouse. ICG dye is a good choice because it is widely available, clinically approved, and it excites and emits in the near infra-red (NIR) portion of the spectrum, which is advantageous in that light scatter is lower and penetration is higher at NIR wavelengths. In one embodiment, a dye consisting of 0.05 ml of 260 uM ICG dye (Cardiogreen, Fluka) is used. In another embodiment, 05 ml of 360 uM of Dextran Texas Red dye (70,000 MW, Invitrogen) can be used.

Other types of second optical contrast substances can also be used, including for example quantum dot agents, IRDye 800, DyLight dyes, Alexa dyes, porphyrin-related dyes, cyanine dyes, active dyes such as pH-sensitive dyes, voltage sensitive dyes, calcium sensitive dyes, dyes which incorporate fluorescent (or Forester) resonance energy transfer properties, dyes with fluorescence or phosphorescence lifetime contrast.

Further, mixtures of one or more optical contrast agents such as mixtures of dyes can also be used as an optical contrast substance.

These dyes can be introduced into or activated in the mouse in a myriad of ways (as can the first optical contrast agent), including for example by injection, intravenously, intraocularly, subcutaneously or intraperitoneally, oral administration, inhalation, rectally, transdermally, using an oxygen bolus, thermal activation, activation of a dye which is already present via introduction of another substance or dye or drug, and so forth.

At process block 36, a targeted image data set of the first optical contrast substance is acquired using the optical detector, preferably while the animal is in the desired arrangement and preferably under anesthesia. The targeted image data set includes a plurality of pixels, with each pixel having an associated intensity value. As used herein, intensity value is meant to encompass one or more components of light measured by the camera, such as grayscale and infrared (IR) components which can be measured by the CCD camera.

If the first optical contrast substance includes a fluorescent substance such as a fluorescent dye, a light source having the appropriate spectral characteristics is applied to excite it. Further, the filter 22 can be tuned so that the light signals recorded by the optical detector for the targeted image set are emitted or absorbed by that fluorescent dye while light outside a predetermined wavelength range is preferably blocked. In other embodiments, a time series of targeted image data sets can also be acquired, as explained below.

At process block 38, a time series of anatomical image data sets of the second optical contrast substance is acquired using the optical detector, preferably while the animal is in the same desired arrangement. This should preferably be performed right after the second optical contrast is introduced. If the second optical contrast agent is a fluorescent dye, a light source having the appropriate spectral characteristics is applied to excite the fluorescent dye. The filter 22 is tuned so that the light signals emitted or absorbed by the dye (in a known predetermined wavelength range) are recorded by the optical detector, and light outside that predetermined wavelength range, such as the excitation light, and emitted light from other contrast substances, is preferably blocked. Thus, each anatomical image data set is acquired at a selected time, and includes a plurality of pixels, with each pixel having an associated intensity value.

The time range over which the time series is obtained can be selected depending on the optical contrast substance that is used. In one example, a time range on the order of 40 minutes may be used, or a time range on the order of 20-30 seconds may be used. Different dyes or other optical contrast substances will have different time courses in different anatomical structures, and different anatomical structures can be emphasized depending on the time range selected. For example, a dye may clear very quickly through an organ such as the brain and take a long time to build up in adipose tissue, and these characteristics can be exploited by the selection of an appropriate time range.

Figure 4:
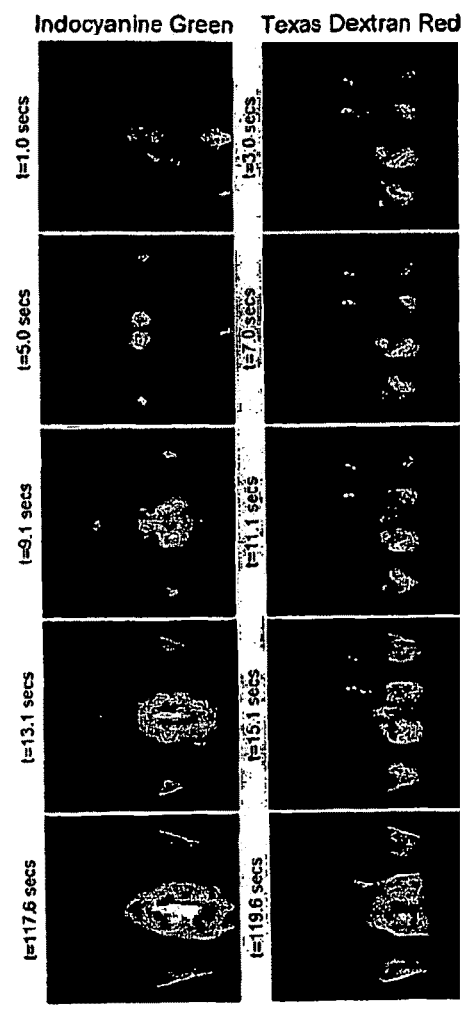
FIG. 4 are time series of images obtained using a mixture of an ICG dye and a Dextran Texas Red dye.

FIG. 4 illustrates a time series of raw fluorescent images following tail vein injection of the ICG dye and Dextran Texas Red dye in a prone mouse, where light sources and filters are sequentially changed so that separate time series image data sets are obtained corresponding to each dye. By 117 seconds after injection, the ICG dye appears to be distributed fairly diffusely throughout the mouse. However, the early images (over just the first 15 seconds) show marked differentiation of different organs. In these images, for example, initially the lungs are bright, representing the initial circulation of the dye passing from the tail vein to the heart's right ventricle and through the lungs before reaching the rest of the body. Next, bright signal is seen in the brain, kidneys, spleen and spine corresponding to flow out of the left ventricle of the heart through the ascending and descending aortas.

The Dextran Texas Red dye shows an initial non-zero value, likely owing to intrinsic autofluorescence in the large intestine at similar wavelengths.

Although not shown here, but demonstrated in preliminary data, over longer timescales, differences in the clearance and metabolism of this and other dyes in different organs may also provide distinct dynamic contrast. Further, longer timescales can also illustrate additional physiologically reasonable trends such as for example, late uptake by adipose tissue, remaining high after 25 minutes, a rapid and sustained uptake by the liver, and fast disappearance from the brain region (ICG is not expected to cross the brain barrier). The utilization of useful organ-specific dynamics over both short and long timescales is an important feature of this dynamic molecular imaging method.

As stated above, the order of the steps shown in this flow chart can be varied. For example, the order of the steps 30, 32, 34, 36, and 38 is not material (except that an animal needs to be positioned in the field of view of the optical detector prior to when imaging occurs). The introduction or activation of the first optical contrast substance can occur prior to or after the introduction or activation of the second optical contrast substance, and each of these can occur prior to or after the time when the animal is positioned in the field of view of the optical detector. Further, in certain embodiments it may be desirable to first introduce or activate and acquire images of one of the optical contrast substances prior to the introduction or activation and imaging of the other optical contrast substance. Also, the order of these two data acquisition steps does not always matter. Note that image data sets corresponding to the first optical contrast substance and to the second optical contrast substance may be interleaved in time by switching between different excitation wavelengths and switching between appropriate predetermined ranges by appropriately tuning the filter 22. Because both image data sets are acquired with the mouse in the same desired arrangement, true co-registration of these different image data sets is possible. Depending on the types of the optical contrast substances used, and the capability of the optical detector in terms of light components that can be recorded, it is possible for these steps to be performed simultaneously, although they can also be performed separately.

Preferably, a grayscale bright-field image data set of the mouse can also be acquired, and used as a further co-registered data set providing additional localization information in an anatomical image map.

At process block 40, the anatomical image data sets are analyzed to extract a plurality of anatomical structures. At process block 42, an anatomical image map is generated showing the delineated anatomical structures. These so called spatiotemporal steps can be performed in a number of ways, as described more fully below. Ideally, individual anatomical structures such as organs are identified and delineated based on their different patterns of ICG fluorescence. The raw light signals measured are typically mixtures, since skin, with its own ICG time-course behavior, overlies all the internal organs. Moreover, of course, organs themselves can be located with respect to each other and relative to the camera such that mixed time courses are present at the surface. The signals corresponding to each organ thus have to be disentangled.

Figure 5:
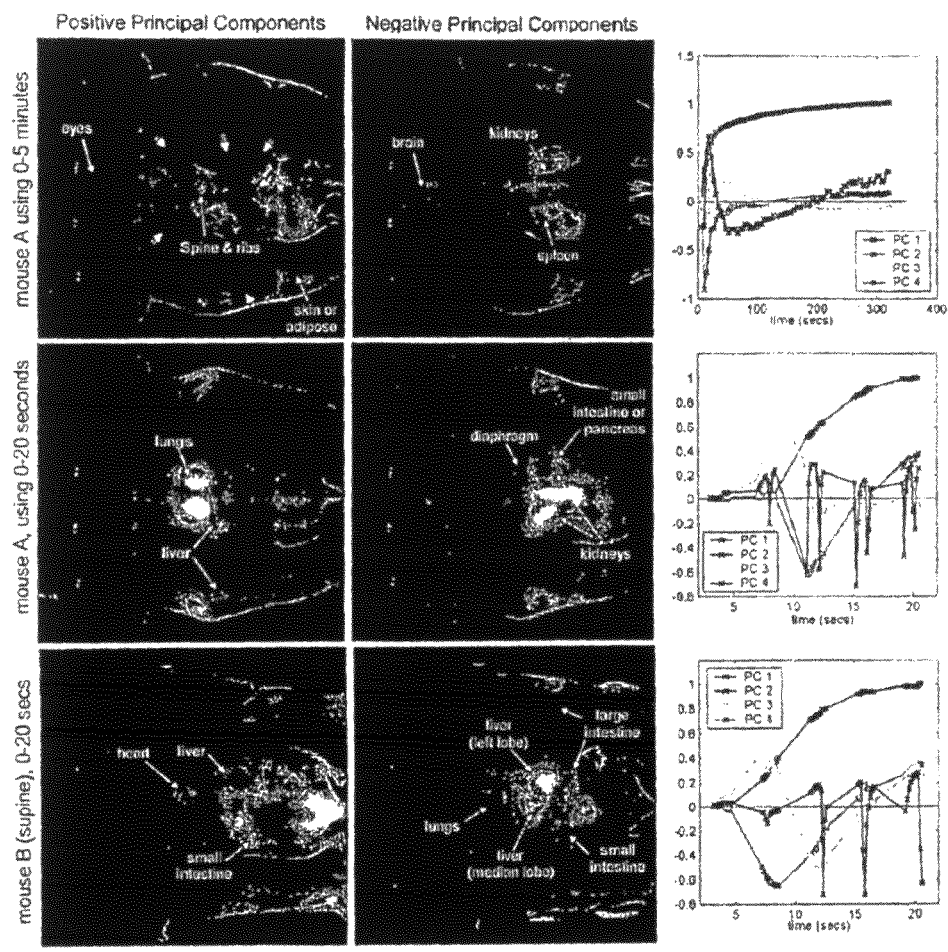
FIG. 5 is an example of a principal component analysis.

The image processing and data analysis can be performed with the aid of MATLAB software functions such as a principle component analysis (PCA) and a non-negative least squares fit. One embodiment performs a principal component analysis on the image data sets, by seeking the major orthogonal temporal variations in the series, and generating images from these components. The first principal component is typically the mean image and time course. The second, third and fourth components correspond to the next three most significant temporal trends in the data. For example, FIG. 5 illustrates the second, third and fourth components as red-green-blue (RGB) image merges of both their positive and negative going structure, which is overlaid onto a faint bright field image of the mouse for orientation. The corresponding time courses for these components are also shown. Thus for each time course, a set of the spatial pixels corresponding to the time course is produced, identified and visualized. In this case, twenty second data sets for prone and supine positions were used. Note that the two sets of time courses on the right have similar characteristics. The spikes in the fourth component correspond to breathing related motion.

While PCA is effective in delineating anatomical structures that can initially be identified, PCA may also be sensitive to noise and the composition of the data, such that the sign, order and composition of the first several temporal orthogonal components may vary from one animal to the next.

Thus another method for analysis relies on the biodistribution dynamics of the organs themselves, with trends that might be consistent and repeatable. For example, a set of basis time-courses which are suitably unique can be generically developed or extracted from the acquired data set. In one embodiment, specific regions of interest of the anatomical image data sets which are thought to be organs can be identified, and their respective time courses extracted therefrom. For example, these regions can be identified from initial PCA procession or using an overlay of a standard anatomical atlas whose regions can then also be iteratively refined based on the temporal analysis. In other embodiments, a priori information regarding likely time courses for various organs are provided, which information is known from a thorough characterization of the dye. Since dynamic contrast is a direct result of each organ's different physiological properties and is therefore likely to be a specific signature, at least in healthy animals of similar ages, such a priori information may provide reliable results. If inter-animal variation is found to be too substantial, a set of rules may be developed (for example, lungs respond first, liver remains elevated after 5 minutes, etc.) which are applied to each data set to extract animal-specific basis time courses. Once a basis set of temporal signatures is obtained, these can be spatially mapped using a straightforward non-negative least squares fit. More specifically, the time courses ($T_{org1}(t)$, $T_{org2}(t)$, . . . ) can then be used in a linear non-negative least-squares fit to the image time series data $M(r,t)$ to resolve the spatial distribution of pixels r with that time course ($I_{org1}(r)$, $I_{org2}(r)$, according to solving the following:

$$M(r, t) = [I_{org1}(r) \quad I_{org2}(r) \quad \ldots \quad I_{orgN}(r)] \begin{bmatrix} T_{org1}(t) \\ T_{org2}(t) \\ \ldots \\ T_{orgN}(t) \end{bmatrix}$$

Figure 6:
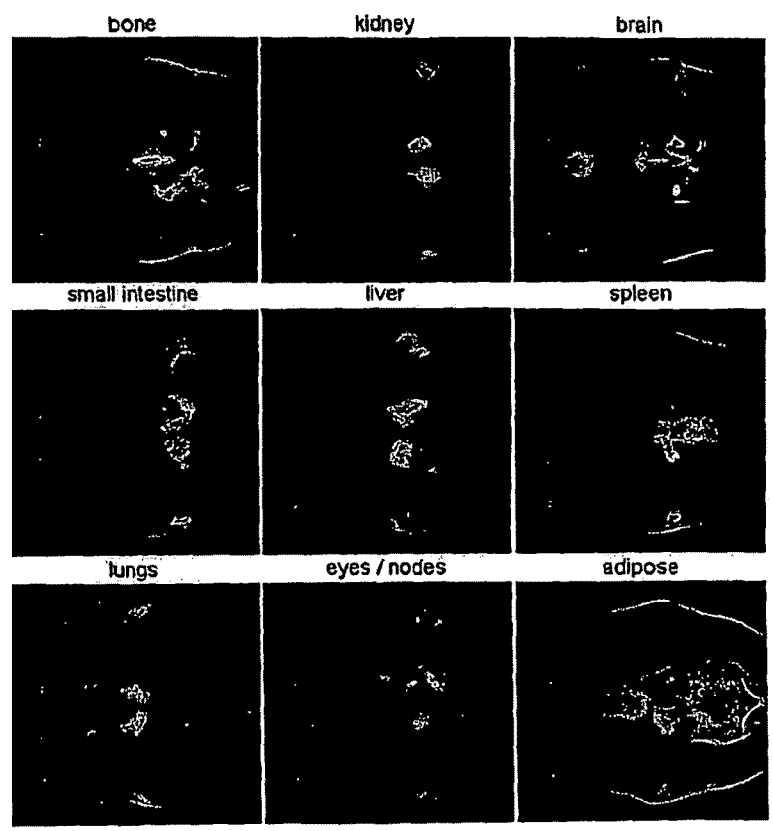
FIG. 6 are examples of images of extracted anatomical structures overlaid with a faint bright field image.

FIG. 6 shows the results of a spatiotemporal fit performed on the ICG data from one mouse over 25 minutes, using nine time courses. Pixel sets corresponding to each of nine anatomical structures are generated and identified, corresponding to bone, kidney, brain, small intestine, liver, spleen, lungs, eyes/nodes, and adipose tissue. The mean residuals of this fit were very small (<1.3%) suggesting that most temporal variance in the data set was accounted for by the basis time courses. Here an initial PCA analysis is used to guide selection of regions, and the basis time courses (Tn(t)) were extracted from the raw data. Apart from the first 18 time points, every 4 time points were averaged to create a 94 image long 256×256 pixel image series. Pixel-wise non-negative least squares fits were performed using Matlab to generate nine spatial maps of the pixels whose time courses correlate with the nine basis time courses. These nine pixel sets (An(x, y)) are shown in FIG. 6 overlaid on faint bright-field images.

Once the organs are resolved, an anatomical image map can be generated with these organs combined. In one embodiment, different anatomical structures are delineated by different colors in the generated anatomical image map. An image visualization tool could be used to allow a user to visualize and overlay or merge each component independently or as a composite image. This tool could incorporate 3D visualization and manipulation.

Optionally, at process block 44, the anatomical image map is combined with the targeted image data set to generate an image representative of the animal showing the location of the labeled cells or region with respect to the delineated anatomical structures. Because the generated anatomical image map and the targeted image data set preferably include the same plurality of pixels, this is a simple matter as one image can simply be overlaid on the other.

One advantage of this method is that is does not rely on a complicated 3-D tomographic reconstruction to determine the location of a targeted region, and thus does not require many of the error-prone assumptions that accompany tomography. By imaging and delineating the projection of signals from the various organs as they appear on the surface of the mouse, it is a simple matter to relate these to the internal organs. The mapped organ's surface projection, viewed from 3 or 4 different orthogonal views, should overlay the signal from the second contrast substance if the organ the probe are co-located (assuming the targeted probe and the first optical contrast substance have similar spectral characteristics). For example, if a particular signal from the second optical signal co-localizes with a kidney projection in all views, then that signal must have originated within, and not above or below, that kidney.

In other embodiments, fewer or additional steps may also be performed. For example, improved estimates of the location of a targeted region or labeled cells using multiple views of the mouse and triangulation can also allow an improved quantitative estimation of the concentration of the targeted probe, which can be especially useful in longitudinal studies. The effects of absorption and scattering attenuation can then be corrected for. Also, 3D surface contours of the animal can also be acquired via structured light illumination.

Multispectral imaging can be used to separate signals from one or more dyes from autofluorescent structures and from among themselves using spectral unmixing techniques, typically involving least-squares fitting.

The effects of autofluorescence can also be corrected for using multispectral imaging techniques for obtaining image data sets of various spectral ranges, and using these to subtract out the effects of autofluorescence. A dynamic analysis can also distinguish autofluorescence without the need for multispectral techniques.

Further, the in-vivo dynamics of a dye alone could also be used to elicit a wealth of information about the function and health of the tissues or organs being imaged in a non-invasive manner. For example, since ICG is used clinically to evaluate liver function, a method wherein a time series of images are analyzed as described above could be used to also provide non-invasive measurement of the effects of a drug on the liver. Parts of the body where dye is being washed out can be spatially resolved from parts of the body where dye is accumulating.

The in-vivo dynamics of a targeted optical contrast substance such as a targeted molecular probe itself can also allow enhanced resolution and specificity by applying these same dynamic imaging techniques. For example, if the targeted probe itself changes dynamically (e.g. is activatable or injected intravenously and is dynamically circulating), the probe's dynamics can be exploited to separate it from the confounding effects of steady-state autofluorescence and to separate dye wash-out from dye uptake in truly labeled cells.

For example, another embodiment of a molecular imaging method for generating an image of a targeted region includes acquiring a time series of targeted image data sets of a targeted optical contrast substance within the animal using an optical detector. Each image data set is obtained at a selected time and has the same plurality of pixels, with each pixel having an associated intensity value. The targeted image data sets are analyzed as described above to identify a plurality of distinctive time courses, and a respective pixel set from the plurality of pixels is determined which corresponds to each of the time courses. Each pixel set is associated with an identified structure. An image of the animal is generated wherein a targeted region is delineated using the identified structures. For example, the targeted region could be delineated by subtracting one or more identified structures from the final image data set, or the targeted region could be one of the identified structures.

Figure 7:
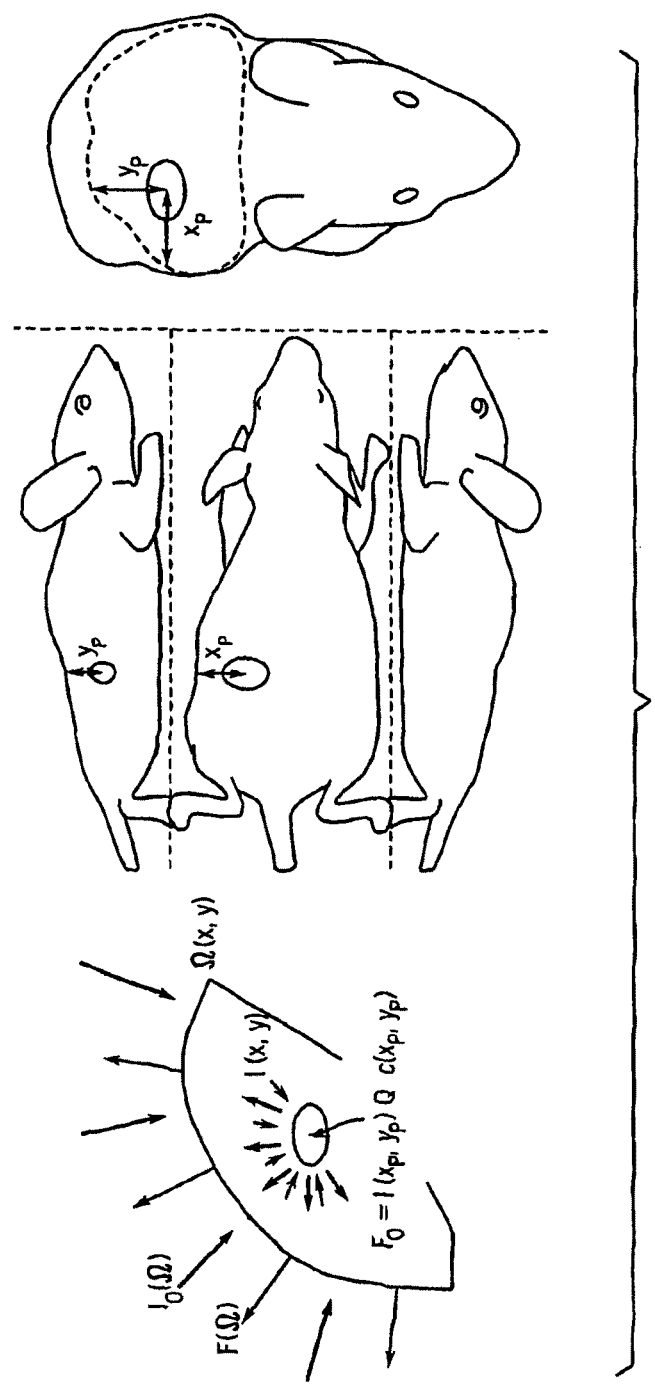
FIG. 7 shows a schematic of the illumination geometry of a localized molecular probe on the left (as measured in a system such as shown in FIG. 1), and the localization of the lesion based on three views on the right.

In other embodiments, a step of deriving quantitative measurement accuracy information from an organ using the identified anatomical structures can also be performed. For example, FIG. 7 shows a schematic of the illumination geometry of a localized molecular probe as measured in imaging system 10. Light $I_0(\Omega)$ is incident on the boundary $\Omega(x,y)$ and travels through the tissue towards a localized fluorophore as $I(x,y)$. The true fluorescence of the fluorophore $F_o$ is a function of its quantum yield (Q), its illumination intensity $I(x_p, y_p)$ and its concentration $c(x_p,y_p)$, or spatially distributed: $c(x+\Delta x, y+\Delta y)$ which is the value it is desired be recovered. Therefore, in this simplified case, the measurement can be considered to correspond to the following equation:

$$F(\Omega) = I(x_p+\Delta x, y_{p+\Delta y}) \times Qc(x+\Delta x, y+\Delta y) \times L(x_{p+\Delta x \to \Omega, yp} + \Delta y \to \Omega)$$

If the locations of $x_p, y_p$ and the shape of $\Omega$ are known, the excitation light distribution $I(x,y)$ can be modeled using simulations such as Monte Carlo modeling, based on estimates of the absorbing $\mu_a^{ex}(x,y)$ and scattering properties $\mu_s^{ex}(x,y)$ of the tissue encountered, and the initial illumination distribution $I_0(\Omega)$. A measure of $I_0(\Omega)$ can be obtained by imaging the diffuse reflectance $DR(\Omega)$ of the excitation light (with a scaling factor proportional to the isotropy of back-scatter, which we assume will stay constant). Light emitted from the fluorophore experiences losses from absorption $\mu_a^{em}(x,y)$ and scattering $\mu_s^{em}(x,y)$ given by $L(x_p \to \Omega, y_p \to \Omega)$, and is then measured as it exits the tissue as $F(\Omega)$. These losses can also be simulated using estimates of tissue $\mu_a^{em}(x,y)$ and $\mu_s^{em}(x,y)$. Therefore by measuring $F_o(\Omega)/DR(\Omega)$, and simulating $I(x,y)/I(\Omega)$ and $L(x_p \to \Omega, y_p \to \Omega)$, improved estimates of $c(x,y)$ can be made without utilizing a full image reconstruction process. It is believed that the $x_p, y_p$ can be estimated from the 3-face views of the mouse as illustrated in the right side of FIG. 7. If the surface interpolated from these views is insufficient to generate $\Omega$ a surface rendering measurement can be performed. This is one examples of a plurality of approaches whereby multi-view anatomical data can be incorporated into analysis of images of optical contrast substances to improve quantitative estimates of their location and properties.

In standard methods $\mu_a^{ex}(x,y)$, $\mu_s^{ex}(x,y)$, $\mu_a^{em}(x,y)$ and $\mu_s^{em}(x,y)$ are often assumed to be constant, and have been previously estimated. However, there is significant heterogeneity in the body that can cause different attenuation depending on the relative position of the localized targeted optical contrast substance. For example, the liver is highly attenuating to visible wavelengths, so a lesion positioned under a lobe of the liver will have distorted values of $c(x,y)$. Other improvements can be obtained by incorporating an anatomical image map into the above method to compensate for spatially varying differences in absorption and scatter experienced by fluorescence depending on its position relative to major organs. This method, combined with the ability to estimate of $x_p, y_p$, (both of which can be specific to each measurement and therefore overcome the effects of an animal gaining weight or being positioned differently), is expected to provide improved longitudinal quantification accuracy without the complexity of obtaining and reconstructing full 3D optical tomographic measurements.

Figure 8:
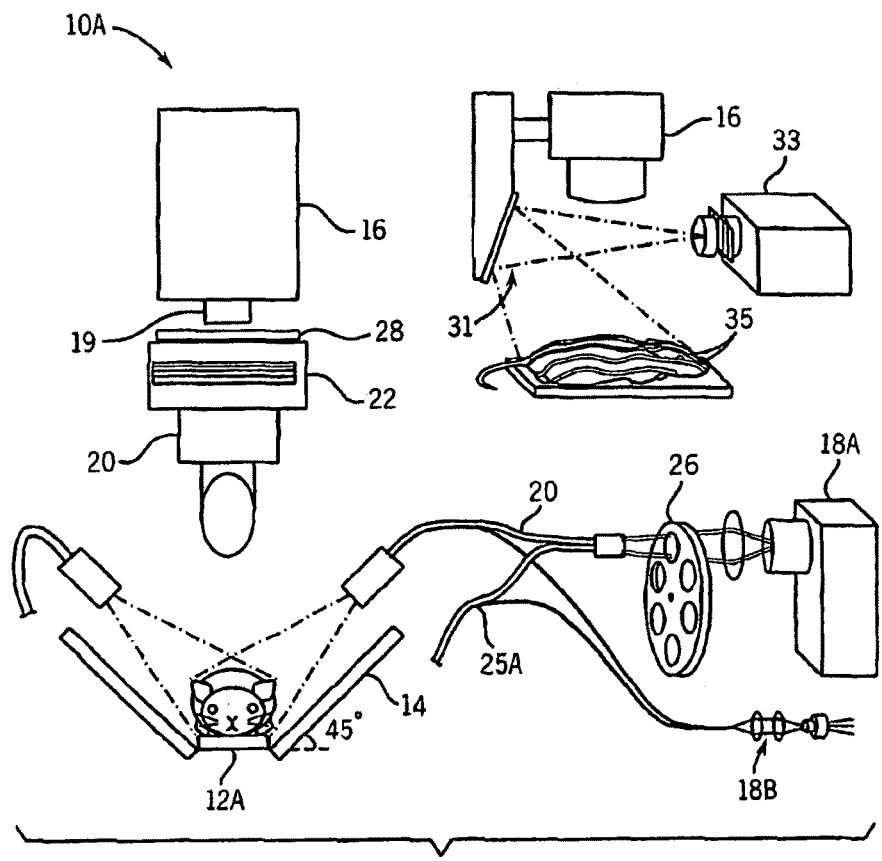
FIG. 8 is another embodiment of an imaging system that can be used with the methods described herein.

FIG. 8 illustrates another embodiment of an imaging system 10A also including a processor and display device (not specifically shown). This imaging system 10A incorporates automated multi-wavelength excitation via a filter wheel 26, and emission via a liquid crystal tunable filter 22. Light source 18A is preferably a halogen light source, but light emitting diodes or laser diodes can also be used. An automated variable attenuator 28 is also included. The animal can be positioned on a glass platform 12A with mirrors 14 enabling imaging of multiple views. Bifurcated light-guides 25A can be used. The inset of FIG. 8 shows a mirror 31 positioned to allow simultaneous patterned illumination of the mouse using a digital projector 33. By projecting a pattern such as parallel lines 35 of light onto a curved surface and imaging from three sides, the contours of the surface can be rendered.

There exist a broad range of approaches to the spatiotemporal analysis of dynamic images to allow delineation of regions, or extraction of timecourses.

For example, an algorithm could be used to identify major timecourses represented within the pixels of the dynamic data set (e.g. singular value decomposition, independent component analysis or principle component analysis, such as discussed above).

A user or intelligent algorithm could extract 'seed' regions of the images, whose timecourses can be used in a least-squares or other fitting step to identify pixels with similar temporal characteristics.

A 'basis set' of timecourses expected to be characteristic of various tissue, organs or structures for a particular dye could be fitted to acquired data (these timecourses could be extracted from this data or a different data set from the same animal or other animals).

Blind-source separation and other automated analysis steps could be applied which seek regions of interest.

A-priori information from a prior analysis step, prior dye, an anatomical atlas, or physiological parameters could be incorporated into the algorithm.

The algorithm could be iterative, and use a plurality of methods to improve estimates of the locations of organs or areas of interest, perhaps by using basic timecourses, identifying regions and then extracting the true timecourse of those regions and fitting again and so-on.

The multi-view nature, 3D projections or surface rendered data could be incorporated into the analysis step.

The dynamic imaging data may be acquired at multiple wavelengths: for multiple excitation, or multiple emission wavelengths even if only a single optical contrast substance is used. Such multispectral data is known to allow delineation of structures based on the differing spectra of autofluorescence versus exogenous optical contrast substances. The spectral properties of such substances can also change when they are in different organs or tissues (perhaps owing to temperature, pH etc). It is possible that analysis could incorporate both multi-spectral and dynamic delineation, either as separate steps, or incorporated into a combined algorithm which exploits both sources of contrast.

If multiple optical contrast substances are used, their dynamic behavior could be incorporated into the same multi-parameter algorithm to extract useful information.

The fluorescence lifetime, phosphorescence decay or other physical property of the dye could also be measured dynamically, and its changes be used to delineate useful anatomical structures.

Algorithms have been developed to allow automated or user-assisted multispectral delineation from a stack of images representing different spectral characteristics of in-vivo optical contrast substances. Such algorithms can also be applied to dynamic imaging analysis.

Many medical imaging processing methods have been developed for so-called 'perfusion imaging', e.g. in MRI and x-ray CT. Perfusion imaging seeks to delineate structures, organs and tissues from the dynamics of an injected contrast agent. Such algorithms could be applied to the analysis of dynamic optical data.

Optical tomography utilizes optical measurements to generate a 3D map of the internal optical contrast structure of an object. It has been shown that it is possible to incorporate a-priori information into such reconstructions such as spectral, spatial and temporal priors, which can improve image reconstruction performance. The temporal dynamics of anatomical structures from dynamic optical imaging could be incorporated into 3D optical tomography reconstructions to improve imaging performance. The delineation step of separating anatomical structures based on their dynamic behavior could be incorporated into a 3D reconstruction, such that the result could be a 3D map of the internal anatomical structures of the animal.

Dynamic imaging could be applied to the imaging of humans (infant or adult). Anatomical mapping using ICG may be feasible in small infants, and may also allow organ function to be non-invasively evaluated. Laparoscopic, endoscopic or otherwise non-invasive or intra-surgical embodiments of dynamic optical imaging could be used, for example, to delineate anatomical structures or disease perimeters in-vivo.

In summary, exploiting the dynamics of optical contrast substances such as fluorescent probes in animals is an elegant and simple way to significantly enhance optical imaging performance and contrast.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

What is claimed is:

1. An in-vivo optical molecular imaging method for producing an image of an animal, comprising:
    acquiring, from an animal positioned on an imaging platform, a time series of image data sets of a targeted optical contrast substance within the animal, the time series obtained by taking a plurality of images at distinct times following introduction of the contrast substance into the animal, using an optical detector, wherein each image data set is obtained at a selected time and has the same plurality of pixels, with each pixel having an associated value for each time in the time series, the imaging platform having a surface for supporting the subject in a desired arrangement in a field of view of an optical detector operable to acquire an image of a subject within the field of view,
    and wherein at least one mirror is arranged at an angle with respect to the imaging platform surface such that multiple views of the subject are within the field of view of the optical detector, and
    wherein a processor is configured to process image data received from the optical detector;
    determining a plurality of distinctive time courses based on the image data sets,
    analyzing the image data sets to separate, for each pixel of a plurality of pixels, the associated values into a plurality of components, each of which is associated with one of the time courses, and
    generating an image of the animal wherein the value at each pixel of the generated image corresponds to the value of the component associated with a single time course,
    wherein time courses are $(T_{org1}(t), T_{org2}(t), \ldots)$ and the time courses are used in a linear non-negative least-squares fit to image time series data $M(r,t)$ to resolve spatial distribution of pixels r with t time course $(I_{org1}(r), I_{org2}(r))$, by solving:

$$M(r, t) = [I_{org1}(r) \ I_{org2}(r) \ \ldots \ I_{orgN}(r)] \begin{bmatrix} T_{org1}(t) \\ T_{org2}(t) \\ \vdots \\ T_{orgN}(t) \end{bmatrix},$$

and wherein the steps of acquiring, determining, analyzing and generating are performed on a machine-readable medium that includes instructions executable by the processor.

2. The method of claim 1, wherein the optical contrast substance is a dye.

3. The method of claim 1, wherein the analyzing step includes a principal component analysis.

4. The method of claim 1, wherein the analyzing step includes using a plurality of basis time courses in a least squares determination of a matrix equation relating the image data sets to the basis time courses.

5. The method of claim 1, further including determining autofluorescent effects and subtracting the autofluorescent effects to generate the image of the animal.

6. The method of claim 1, wherein a field of view of the optical detector includes multiple views of the animal.

7. The method of claim 1, wherein the step of acquiring a time series of image data sets comprises acquiring a time series of image data sets of a plurality of targeted optical contrast substances.

8. The method of claim 1, wherein the step of determining a plurality of time courses includes using pixel values from multiple time points within the time series, and the generating step further comprises calculating a single spatial distribution of the pixel values across the time series.

9. The method of claim 1, wherein the step of analyzing the image data sets is achieved using pixel values obtained at a plurality of time points within the time series such that the plurality of time courses are identified based on calculated spatial and temporal patterns of emission from the optical contrast substance.

10. The method of claim 1, wherein the step of determining a plurality of time courses is a calculation based on the temporal pattern of emission of the optical contrast substance at each pixel.

11. The method of claim 1, wherein the optical contrast substance within the animal are used to identify multiple organs within a single image.

12. The method of claim 1, wherein the method further includes:
    associating at least one respective pixel set with a physiological process.

13. The method of claim 1, wherein the optical contrast substance in the animal separates targeted optical contrast substance wash-out from targeted optical contrast substance uptake.

14. The method of claim 1, wherein the determining step is performed based on the time series of image data sets obtained from the animal.

15. The method of claim 1, wherein the determining step is performed based on a time series of image data sets obtained from an animal that is different from the animal to be imaged.

16. An in-vivo optical molecular imaging method for localizing a targeted region with respect to anatomical structures of an animal, comprising:
positioning the animal on an imaging platform having a surface for supporting the subject in a desired arrangement in a field of view of an optical detector operable to acquire an image of a subject within the field of view,
wherein at least one mirror is arranged at an angle with respect to the imaging platform surface such that multiple views of the subject are within the field of view of the optical detector, and
wherein a processor is configured to process image data received from the optical detector;
acquiring a targeted image data set of a first dye using the optical detector while the animal is in the desired arrangement, the targeted image data set having a plurality of pixels,
acquiring a time series of anatomical image data sets of a second dye using the optical detector while the animal is in the same desired arrangement, the time series obtained by taking a plurality of images at distinct times following introduction of the contrast substance into the animal, each anatomical image data set obtained at a selected time and having a same plurality of pixels as the others, each pixel having an associated value for each time in the series,
determining a plurality of distinctive time courses based on the dynamics of the image data sets of the second dye in the animal,
analyzing the anatomical image data sets to separate, for each pixel of a plurality of pixels, the associated values into a plurality of components, each of which is associated with one of the time courses, and associating each time course with an identified anatomical structure,
generating an anatomical image map of the animal which includes each anatomical structure as a differentiated pixel set, and
combining the targeted image data set with the anatomical image map to generate an image representative of the animal showing the location of the targeted region with respect to the anatomical structures,
wherein time courses are ($T_{org1}(t)$, $T_{org2}(t)$, . . .) and the time courses are used in a linear non-negative least-squares fit to image time series data $M(r,t)$ to resolve spatial distribution of pixels r with t time course ($I_{org1}(r)$, $I_{org2}(r)$, by solving:

$$M(r, t) = [I_{org1}(r)\; I_{org2}(r)\; \ldots\; I_{orgN}(r)] \begin{bmatrix} T_{org1}(t) \\ T_{org2}(t) \\ \vdots \\ T_{orgN}(t) \end{bmatrix}.$$

17. The method of claim 16 wherein the acquiring steps include the use of optical filters to distinguish between the first dye and the second dye.

18. The method of claim 16, wherein the analyzing step includes using a plurality of basis time courses in a least squares determination of a matrix equation relating the anatomical image data sets to the basis time courses to determine a pixel set corresponding to each of the plurality of basis time courses, and to identify specific anatomical structures corresponding to each pixel set.

19. An imaging system, comprising:
an optical detector which is operable to acquire an image of a subject within a field of view;
an imaging platform having a surface for supporting the subject in a desired arrangement;
at least one mirror arranged at an angle with respect to the imaging platform surface such that multiple views of the subject are within the field of view of the optical detector,
a processor configured to process image data received from the optical detector, and
a machine-readable medium that includes instructions executable by the processor, the instructions including
acquiring a time series of image data sets of a targeted optical contrast substance within the subject using the optical detector, the time series obtained by taking a plurality of images at distinct times following introduction of the contrast substance into the animal, and wherein each image data set is obtained at a selected time and has the same plurality of pixels, with each pixel having an associated value for each time in the time series,
determining a plurality of distinctive time courses based on the image data sets,
analyzing the image data sets to separate, for each pixel of a plurality of pixels, the associated values into a plurality of components, each of which is associated with one of the time courses, and
generating an image of the subject wherein the value at each pixel of the generated image corresponds to the value of the component associated with a single time course, and
wherein time courses are ($T_{org1}(t)$, $T_{org2}(t)$, . . .) and the time courses are used in a linear non-negative least-squares fit to image time series data $M(r,t)$ to resolve spatial distribution of pixels r with t time course ($I_{org1}(r)$, $I_{org2}(r)$, by solving:

$$M(r, t) = [I_{org1}(r)\; I_{org2}(r)\; \ldots\; I_{orgN}(r)] \begin{bmatrix} T_{org1}(t) \\ T_{org2}(t) \\ \vdots \\ T_{orgN}(t) \end{bmatrix}.$$

20. The imaging system of claim 19, wherein two mirrors are arranged at an angle with respect to the imaging platform surface.

21. The imaging system of claim 19, wherein each mirror is arranged at a forty five degree angle with respect to the imaging platform surface.

22. An in-vivo optical molecular imaging method for producing an image of an animal, comprising:
acquiring, from an animal positioned on an imaging platform, a time series of image data sets of a targeted optical contrast substance within the animal, the time series obtained by taking a plurality of images at distinct times following introduction of the contrast substance into the animal, using an optical detector, wherein each image data set is obtained at a selected time and has the same plurality of pixels, with each pixel having an associated value for each time in the time series, the imaging platform having a surface for supporting the subject in a desired arrangement in a field of view of an optical detector operable to acquire an image of a subject within the field of view, and wherein at least one mirror is arranged at an angle with respect to the imaging platform surface such that multiple views of the subject are within the field of view of the optical detector, and wherein a processor is configured to process image data received from the optical detector;

determining a plurality of distinctive time courses based on the image data sets, analyzing the image data sets to separate, for each pixel of a plurality of pixels, the associated values into a plurality of components, each of which is associated with one of the time courses, and generating an image of the animal wherein the value at each pixel of the generated image corresponds to the value of the component associated with a single time course, and, after the determining steps and the analyzing steps, generating an anatomical image map of the animal which includes each anatomical structure as a differentiated pixel set, and combining the targeted image data set with the anatomical image map to generate an image representative of the animal showing the location of the targeted region with respect to the anatomical structures, wherein the steps of acquiring, determining, analyzing and generating are performed on a machine-readable medium that includes instructions executable by the processor.

* * * * *